United States Patent [19]

Cuda

[11] Patent Number: 4,846,546
[45] Date of Patent: Jul. 11, 1989

[54] FIBER OPTIC LIGHT CARRYING CURING PROBE

[76] Inventor: Joseph Cuda, 2937 Christopher Creek Rd. North, Jacksonville, Fla. 32217

[21] Appl. No.: 192,358

[22] Filed: May 10, 1988

[51] Int. Cl.⁴ .............................................. G02B 6/04
[52] U.S. Cl. ................................................ 350/96.24
[58] Field of Search ........................... 350/96.24, 96.25

[56] References Cited

U.S. PATENT DOCUMENTS

| | | | |
|---|---|---|---|
| 2,825,260 | 3/1958 | O'Brien | 350/96.25 |
| 3,148,967 | 9/1964 | Hicks, Jr. | 350/96.25 X |
| 3,666,949 | 5/1972 | De Falco et al. | 350/96.24 X |
| 3,742,107 | 6/1973 | Hawkins | 350/96.24 X |
| 3,814,618 | 6/1974 | Kimpel et al. | 350/96.24 X |

OTHER PUBLICATIONS

Demetron Corp. Catalogue, in pertinent part.

Primary Examiner—John D. Lee
Assistant Examiner—Phan T. Heartney
Attorney, Agent, or Firm—Banner, Birch, McKie & Beckett

[57] ABSTRACT

A fiber optic light carrying probe for efficiently transmitting high intensity light from a high intensity light source to a point of application is provided with unsheathed glass cladding which prevents light leakage along the length of the probe. When the probe is used in orthodontic procedures, such as bonding, the cladding averts the high intensity light from the patient's eyes which would otherwise cause discomfort. Furthermore, the probe may be repeatedly autoclaved without significantly damaging or deteriorating the glass cladding.

25 Claims, 1 Drawing Sheet

FIBER OPTIC LIGHT CARRYING CURING PROBE

BACKGROUND OF THE INVENTION

This invention relates to fiber optic light carrying probes and more particularly to a light carrying probe suitable for curing resins in medical, scientific, industrial amd military applications. The probe is also suitable for providing light during surgical or diagnostic procedures to enhance an operator's perceptions. Thus, the probe also has use in, for example, gynecological procedures.

Resins (restoratives, dental composites and other materials) exposed to high intensity visible light change in form from a paste-like putty to a substance having the hardness of ceramic or glass in a short amount of time. Using this procedure, the standard amount of time to cure restoratives applied to one tooth is approximately ten seconds. The time could be extended, depending on the area and depth of applied restorative, up to sixty seconds. This dental (orthodontic) procedure is relatively new. Generally, the technique is referred to as bonding. By using this technique, which is primarily cosmetic, gaps between the teeth, fillings and cracked or chipped defects can be repaired. Furthermore, color can be matched so that teeth can be restored to their natural look. The teeth (especially the front upper/lower teeth) can also be laminated with a thin layer of this restorative which comes in more than fifty different shades and colors. After hardening (i.e., curing with high intensity light, which is normally provided by fiber optics), the teeth are then reshaped and polished. The probe is not limited, in the medical field, to curing dental resins. For example, it may be used for curing resins used during plastic or reconstructive surgery and in fact may be used in curing most any bone composite.

Originally, the most commonly used fiber optic light carrier was fiber optic cables in lengths from four feet to nine feet, and bundle sizes from 5.0 mm to 7 mm. These cables were plugged into high intensity light sources so that the light would be transmitted through the cable. This apparatus is being gradually replaced by a more practical fiber optic light curing gun coupled to a short fiber optic probe of various lengths and diameters. The probe normally has a bent tip to improve maneuverability in difficult access areas. The gun includes a high intensity fan cooled light source mounted directly inside of the gun enclosure.

The fibre optic probe has been made typically in two different ways. The first involves filling a stainless steel sheath with conventional non-coherent light transmitting glass fibers. This approach is not very effective because the stainless steel tube cannot be adequately packed to produce optimum light transmission. That is, only up to 80% of the tube space can be filled with light transmitting fibers due to, for example, unavoidable gaps between individual fibers.

The second approach produces a sheathed glass cladded fiber optic rod with improved light transmission efficiency. Instead of using conventional fibers to transmit the light, the second approach incorporates a coherent fiber rod. The rod has a packing fraction of over 90% and thus transmits considerably more light than the probe within the scope of the first approach. Improved light transmission, i.e., efficiency, is preferred for a number of reasons. For example, such would reduce curing times. A curing time reduction would, for example, have obvious benefits during dental "bonding" procedures which would include reducing operator fatigue and patient discomfort. To produce the rod, a bundle of large diameter fibers are inserted into clear glass cladding and that assembly drawn to size while heat is applied. During this process, the fibers are fused together while being sealed in the glass cladding. The glass cladded rod is then cut, bent and then sheathed to prevent light leakage along the length of the rod.

The sheathing, which must be capable of withstanding repeated autoclaving due to the obvious need for sterilization before medical use to avoid the transmission of communicable diseases (e.g., AIDS), primarily functions to prevent light leakage. That is, if the high intensity light was allowed to leak from the probe, the operator and operator's assistants could be distracted and thereby error in delicate medical and non-medical procedures. Furthermore, the high intensity light reaching the patient's, operators's or operator's assistant's eyes not only could cause discomfort, but create harmful effects on the physiological make-up of the eye. Thus, even though the sheath increases manufacturing costs, it is evident that it is an essential component of the prior art.

Unfortunately, due to manufacturing considerations, a one-piece sheath is impractical. Stainless steel is appropriate to resolve sterilizing considerations, but inappropriate to sheath a rigid bent rod. First, it would not be feasible to insert the rigid bent glass cladded rod into the rigid stainless steel tube. Furthermore, the difference in melting points between the glass cladded rods and the stainless steel tubing renders the insertion of a given rod into stainless steel tubing, prior to the heating and bending operation, impractical. As a result, high temperature flexible silicon is used to sheath the bent portion, while the straight portion is encased in stainless steel.

Even though the silicon sheath provides rod protection due to its shock absorbing characteristics and survives autoclaving operations better than other suitable elastomers, the silicon sheath design has drawbacks. First, the two-piece sheath construction increases a manufacturer's material acquisition and inventory costs when compared to the requirements for making a glass cladded rod encased within a single piece sheath. Furthermore, the assembly of a two-piece sheath requires more manufacturing steps which can also increase the cost of the probe.

Other drawbacks of the silicon sheath become apparent after repeated sterilization of the probe. That is, the silicon degenerates after repeated autoclaving operations permitting light leakage and inhibiting sterilizability. The silicon sheath shrinks when subjected to the high autoclaving temperatures. Because, the glass cladded rod is rigid, the silicon circumferentially stretches, radially shrinks, develops pockets and gaps, and separates from adjacent probe structure to release the stresses. These pockets, gaps and separations permit light leakage. For example, the fit-up (designated at numeral 25 in FIG. 3) between the silicon sheath and adjacent stainless steel sheath 23 or endfitting 27 degenerates, creating a source for undesirable light leakage. The silicon sheath degeneration also provides a means for trapping bacteria or other infectious matter. For example, because the silicon sheath cannot be permanently sealed to the glass cladding, it is held thereto by friction fit. The silicon sheath then separates from the cladding as it degenerates. The bacteria trapped between the silicon sheath and glass cladded rod, due to the above separation, is not completely removed when the probe is autoclaved. Therefore, the probe becomes a means to transfer communicable diseases (e.g., AIDS) from patient to patient or patient to doctor and so forth. This problem is exacerbated when the probe is used in medical procedures where bleeding is inevitable.

SUMMARY OF THE INVENTION

In view of the above and other deficiencies in the known prior art, it is the aim of the present invention to provide a fiber optic light carrying probe for transmitting high intensity light from a high intensity light source to a point of application which is provided with unsheathed glass cladding that inihibits light leakage along the length of the probe and does not significantly degenerate after autoclaving operations to avoid light leakage and bacteria entrapment problems.

After repeated autoclaving operations, the prior art silicon sheath circumferentially stretches, longitudinally shrinks, and develops pockets and gaps. The degenerated sheath not only allows undesirable and/or harmful high intensity light leakage from the sides of the probe, it provides sites for trapping bacteria or other infectious matter. This bacteria or infectious matter is not necessarily completely removed after the prior art probe is autoclaved.

In further view of the growing problem with infectious diseases transmittable by the use of the prior art instrument (e.g., AIDS), it is another object of the present invention to provide a fiber optic probe which is completely sterilizable thereby making it safe for the dentist or operator, and safe for the patient.

It is a further object of the present invention to provide a fiber optic probe of simple construction which can produce both assembly and material cost savings and therefore increase manufacturing efficiencies. Such is accomplished by eliminating the need to sheath the glass cladding.

Thus, the invention involves sealing large diameter fiber optic quality fibers in a glass cladding which has the property or characteristic of inhibiting light transmission therethrough.

Other important features and advantages of the invention will be apparent from the following description and the accompanying drawings, wherein, for purposes of illustration only, a specific form of the invention is set forth in detail.

DETAILED DESCRIPTION OF THE PREFERRED EMBODIMENTS

Figure 1:
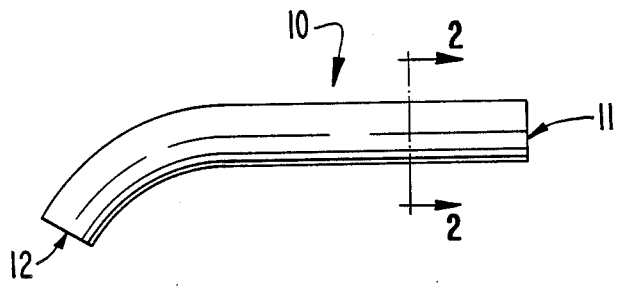
FIG. 1 is a side elevational view of a prior art fiber optic light carrying probe.
Figure 2:
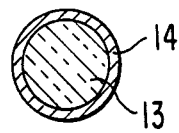
FIG. 2 is a cross-sectional view taken along line 2—2 of FIG. 1.

FIG. 1 depicts a conventional fiber optic probe 10 having a light receiving ends 11 for association with a light source (not shown) and a light emitting end 12. Stainless steel sheath 14 is filled with conventional non-coherent light transmitting glass fibers 13 (see FIG. 2). Sheath 14 may have a bent tip to enhance manipulation and provide access to hard to reach areas. It also may be provided in approximately 3, 4 to 5 inch lengths with an approximately 8 mm inside diameter. Once filled, the probe is ground and polished at each end to obtain maximum light transmission efficiency. However, these probes generally have a low packing fraction, i.e., a maximum of 80%, which limits the amoumt of light that can be transmitted. That is, only up to 80% of sheath 14 can be filled (packed) with the light transmitting fibers. The remaining 20% of non-transmitting space comprises voids between individual fibers and gaps which are normally sealed with high temperature epoxy. Thus, the packing fraction is generally limited to 80%.

Figure 3:
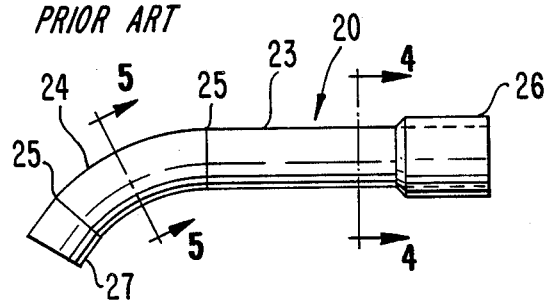
FIG. 3 is a side elevational view of another conventional fiber optic light carrying probe.
Figure 4:
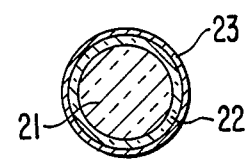
FIG. 4 is a cross-sectional view taken along line 4—4 of FIG. 3.
Figure 5:
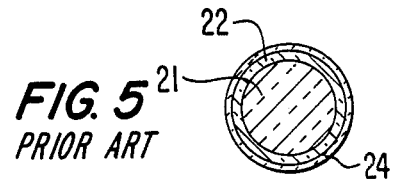
FIG. 5 is a cross-sectional view taken along line 5—5 of FIG. 3.

FIGS. 3–5 show another conventional light transmitting probe having considerably improved transmissivity. Instead of conventional fibers 13, probe 20 incorporates light and image transmitting coherent glass fiber rod 21 encased within clear glass cladding 22. This construction makes a packing fraction of over 90% attainable. Therefore, probe 20 can transmit considerably more light than probe 10. The glass cladded rod may be manufactured by first drawing fiber optic quality glass cladded rod down to approximately 1.0 mm in diameter. These large diameter rod fibers (1.0 mm in diameter) are bunched into a bundles of approximately 38 mm in diameter. Then this bundle of hundreds of large diameter rod fibers is inserted into clear glass cladding (tube of clear sealing glass with an approximately 39 mm inside diameter and an approximately 1.0 mm wall thickness). This glass assembly is drawn into smaller diameter heat fused rods having about an 8 mm diameter and then cut into 3, 4 or 5 inch lengths. These lengths comprise coherent glass fiber rod 21 encased within clear glass cladding 22. The ends of these lengths are ground and polished to maximize transmission. This is especially important to reduce the curing times. As a result of this heat fusion method, gaps between the individual fibers are avoided and high efficiency light transmitting fiber optical cladded rods are produced. These rods may be shaped as desired (e.g., for the intended use). For example, a rod may be heated and bent to give the configuration depicted in the drawings which is suitable for probe manipulation in difficult access areas.

The glass cladded rods are then provided with a sheathing to prevent light leakage along the length of the rod. When the rod is used in orthodontic procedures, such as bonding, the sheath averts the high intensity light from the patient's eyes which could otherwise cause discomfort or permanently harm the physiological make-up of the eye. The sheathing must also be capable of withstanding repeated autoclaving due to the obvious need for sterilization after each use. Consequently, stainless steel tubing makes for an appropriate sheath. However, the glass cladded rod configuration gives rise to further manufacturing considerations with respect to the stainless steel. First, it would not be feasible to insert the rigid bent glass cladded rod into the rigid stainless steel tube. Furthermore, the difference in melting points between the glass cladded rods and the stainless steel tubing renders the insertion of a given rod into stainless steel tubing, prior to the heating and bending operation, impractical. Encasing the straight portion with stainless steel sheath 23 and the bent portion with high temperature silicon sheath 24 resolves these manufacturing problems.

The sheathed glass cladded rods are then provided with endfittings of which stainless steel is again a suitable material. The endfittings are secured to the device with high temperature adhesive to withstand autoclaving. Ring shaped endfitting 27 at the probe's light emitting end protects the probe emitting end. Endfitting 27 also has a circumferential groove (not shown) which provides a mechanism for interchangeably coupling the emitting end to a protective cap (not shown), suitable for shipping and the like, and a light focusing device (not shown). Endfitting 26 is provided at the probe's light receiving end. It is designed for coupling teeth probe to the high intensity light source. For example, endfitting 26 may be configured to fit in the chuck of the VCL 300 gun type light source made by Demetron Research Corporation of Danbury, Conn. The coupling mechanism may also include a groove (not shown) formed in the outer surface of endfitting 26. The coupling mechanism may also include a circumferential groove (not shown) in endfitting 26 for purposes of alignment or enhanced locking.

Figure 6:
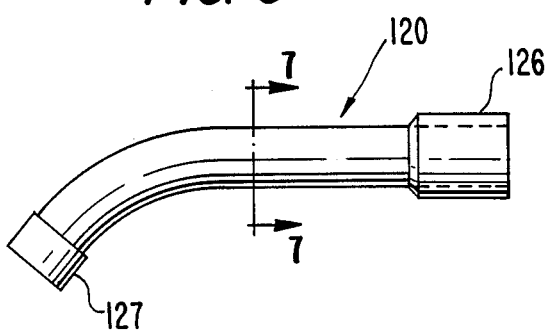
FIG. 6 is a side elevational view of the preferred embodiment of the fiber optic light carrying probe disclosed herein.
Figure 7:
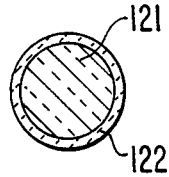
FIG. 7 is a cross-sectional view taken along line 7—7 of FIG. 6.

FIGS. 6 and 7 depict the preferred embodiment of the present invention. Fiber optic light carrying probe 120 prevents light leakage without the need for sheathing the glass cladding. That is, during the drawing and fusing process, when individual 1.0 mm fibers are fused together while being enclosed in a glass cladding tube, glass cladding 122 is selected to have the characteristic or property of inhibiting the transmission of light therethrough. The cladding also protects the fused fibers. Thus, probe 120 incorporates coherent glass fiber rod 121 encased within such light transmission inhibiting glass cladding 122. Blue colored glass cladding performs this function and is preferred due to its aesthetically appealing effect. Furthermore, this blue glass cladding is translucent when activated by high intensity light and therefore is highly complementary to the typical blue light output of most dental light curing guns. The high intensity blue color output results from using a blue color filter mounted at the light part of the gun shaped light source. This filter absorbs undesirable ultraviolet or infrared energy, normally produced by quartz halogen light sources. General Electric, glass type No. 539, soft glass is an example of above colored glass cladding that gives the desired light transmission inhibiting results. However, opaque, translucent, clear colored, translucent colored, black colored or most any colored glass create a similar effect and results including protecting the fused fibers and preventing light leakage while avoiding the bacteria problems related to the silicon sheath prior art design. Furthermore, luminescent effects may be achieved by providing the rod with a ripple finish (e.g., by scratching the rod surface) as opposed to the otherwise flame polished smooth finish.

In sum, improved probe 120 essentially consists only of high temperature solid glass, high temperature epoxy used to secure the stainless steel endfittings 126 and 127 to the probe light receiving and light emitting ends, respectively, and endfittings 126 and 127 which structurally correpsond to previously described endfittings 26 and 27, respectively. This simple construction allows complete and safe autoclaving, resulting in a sterile instrument which retains its light leakage inhibiting properties.

Having described a preferred embodiment in detail, it will be recognized that the foregoing is considered as illustrative only of the principles of the invention. Since numerous modifications and changes will readily occur to those skilled in the art, it is not desired to limit the invention to the exact construction, materials, assembly etc. shown and described. Accordingly, all suitable modifications and equivalents may be resorted to the extent they fall within the scope of the invention and claims appended hereto.

I claim:

1. A fiber optic light carrying probe for transmitting high intensity light from a high intensity light source to a point of application, said probe comprising:
    a coherent glass fiber rod having a light receiving end and a light emitting end, and comprising glass fibers encased within an outer glass cladding, said cladding being unsheathed and defining the outer peripheral surface of the probe; and
    first coupling means at the light receiving end for coupling the probe to the high intensity light source.

2. The probe of claim 1 wherein the cladding comprises translucent glass.

3. The probe of claim 1 wherein the cladding comprises colored glass.

4. The probe of claim 3 wherein the cladding comprises clear colored glass.

5. The probe of claim 3 wherein the cladding comprises translucent colored glass.

6. The probe of claim 3 wherein the cladding comprises black colored glass.

7. The probe of claim 3 wherein the cladding comprises blue colored glass.

8. The probe of claim 7 wherein the cladding comprises General Electric glass type No. 539, soft glass.

9. The probe of claim 1 wherein the cladding comprises opaque glass.

10. The probe of claim 1 wherein said probe emitting end comprises a ring circumscribing a peripheral portion thereof for protecting said probe emitting end.

11. The probe of claim 10 wherein the cladding comprises colored glass.

12. The probe of claim 10 wherein said ring comprises second coupling means for interchangeably coupling said emittng end to a protective cap suitable for protection during shipping and the like, and a light focusing mechanism.

13. The probe of claim 12 wherein said ring and said first coupling means comprise stainless steel.

14. The probe of claim 12 wherein the probe has a first straight segment extending from said receiving end to a second segment having a bend therein.

15. The probe of claim 1 wherein the probe has a first straight segment extending from said receiving end to a second segment having a bend therein.

16. The probe of claim 15 wherein the cladding comprises colored glass.

17. A fiber optic light carrying probe for transmitting high intensity light from a high intensity light source to an application site, and being suitable for curing resins and the like, as well as providing light during surgical and diagnostic procedures, said probe comprising:

a coherent glass fiber rod having a light receiving end and a light emitting end, and comprising glass fibers encased within an outer blue colored glass cladding, said cladding being essentially unsheathed and essentially forming the outermost surface of the probe; and coupling means at the light receiving end for coupling the probe to the high intensity light source.

18. A fiber optic light carrying probe for transmitting high intensity light from a high intensity light source to an application site, and having a substantial bend therein so as to be suitable for curing resins and the like, as well as providing light for surgical and diagnostic procedures, said probe comprising:

a coherent glass fiber rod having a light emitting end including a ringe circumscribing a peripheral portion thereof for protecting said probe emitting end, and a light receiving end including first coupling means circumscribing a peripheral portion thereof for coupling the probe to the high intensity light source, said coherent glass fiber rod comprising glass fibers collectively encased in a single outer glass cladding, said cladding being unsheathed between said ring and said first coupling means and forming the outermost surface of the probe between said ring and said first coupling means.

19. The probe of claim 18 wherein the cladding comprises translucent glass.

20. The probe of claim 18 wherein the cladding comprises colored glass.

21. The probe of claim 20 wherein the cladding comprises clear colored glass.

22. The probe of claim 20 wherein the cladding comprises black colored glass

23. The probe of claim 20 wherein the cladding comprises blue colored glass.

24. The probe of claim 23 wherein the cladding comprises General Electric glass type no. 539, soft glass.

25. The probe of claim 18 wherein the cladding comprises opaque glass.

* * * * *